United States Patent [19]

Ogilvie

[11] Patent Number: 4,868,187
[45] Date of Patent: Sep. 19, 1989

[54] ANTI-VIRAL N-SUBSTITUTED PYRIMIDINES

[75] Inventor: Kelvin K. Ogilvie, Candiac, Canada

[73] Assignee: Syntex (U.S.A.) Inc., Palo Alto, Calif.

[21] Appl. No.: 23,582

[22] Filed: Mar. 9, 1987

Related U.S. Application Data

[60] Division of Ser. No. 302,790, Sep. 16, 1981, which is a continuation-in-part of Ser. No. 187,631, Sep. 16, 1980, Pat. No. 4,347,360.

[51] Int. Cl.$^4$ ............... A61K 31/505; C07D 239/30; C07D 239/47; C07D 239/55
[52] U.S. Cl. ..................... 514/269; 514/245; 514/274; 544/194; 544/229; 544/211; 544/313; 544/314; 544/317
[58] Field of Search ............... 544/313, 314, 317, 194, 544/229, 211; 514/274, 245, 269

[56] References Cited

U.S. PATENT DOCUMENTS

| | | | |
|---|---|---|---|
| 4,146,715 | 3/1979 | Schaeffer | 544/276 |
| 4,171,431 | 10/1979 | Skulnick | 544/194 |
| 4,501,744 | 2/1985 | Ogilvie | 544/211 |
| 4,508,898 | 4/1985 | Ogilvie | 544/211 |

OTHER PUBLICATIONS

Ogilvie et al., CA 100-192208b.
Martin et al., CA 102-95995q.
Ogilvie, CA 103-71626q.
Takaku et al., CA 108-204992h.

Primary Examiner—Cecelia Shen
Attorney, Agent, or Firm—David A. Lowin; Tom M. Moran

[57] ABSTRACT

Nucleoside analogues having a ring-open structure, of general formula:

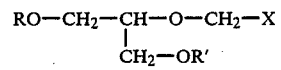

where R and R' may be hydrogen, silyl groups, substituted alkyl groups, benzyl groups and the like, and X is an optionally substituted base such as guanine or adenine, have been shown to exhibit anti-viral and other biological acivities at non-toxic levels.

7 Claims, No Drawings

ANTI-VIRAL N-SUBSTITUTED PYRIMIDINES

This is a division of pending application Ser. No. 302,790, filed Sept. 16, 1981, which is a CIP of U.S. Ser. No. 187,631 for Sept, 16, 1980, now U.S. Pat. No. 4,347,360, incorporated herein by reference.

BACKGROUND OF THE INVENTION

This invention relates to novel compositions and chemical compounds and processes for their preparation. More particularly, it relates to novel ring-open nucleoside and nucleotide analogues and the like, which show bioregulation activity, e.g. antiviral activity and processes for their synthesis.

BRIEF REFERENCE TO THE PRIOR ART

Nucleosides comprise a D-ribose or 2-deoxy-D-ribose sugar unit, chemically bonded to a purine or pyrimidine base selected from adenine, cytosine, guanine, thymine and uracil, via a nuclear nitrogen atom of the base. Since they are units of nucleic acids found naturally in living cells, it has been speculated previously that nucleosides and nucleotides and their related analogs might have potential as chemotherapeutic agents. Any practical value they may have, however, is often greatly reduced by their ready deamination in vivo by deaminases. Stuides have been conducted to determine the relationship between structure and activity for both substrates and inhibitors of adenosine deaminase, some such studies involving ring-opened analogues of nucleosides. To date, however, despite several promising reports of novel compounds, no such compounds have been produced and developed for chemotherapeutic use, with the possible exception of a-cycloguanosine, described in U.S. Pat. No. 4,146,715 Schaeffer.

SUMMARY OF THE INVENTION

The present invention relates to antivirally active dinucleotide and nucleoside analogues, processes for their preparation, and pharmaceutically acceptable compositions thereof for administration to mammals to treat viral infections. The nucleoside analogues of the present invention are N-substituted purine and pyrimidine compounds corresponding to the general formula:

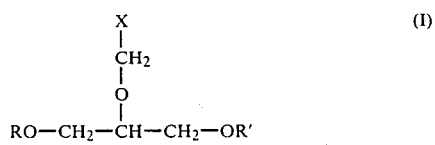

wherein X represents a uracil group, a 5-fluorouracil group, a cytosine group, a 5-azacytosine group, an adenine group, a guanine group or a 2-N-acetylguanine group; and R and R' are independently selected from hydrogen, benzyl and tert.butyldimethylsilyl, with the proviso that, when X represents an adenine group, at least one of R and R' represents other than hydrogen.

It will be appreciated that the compounds according to the present invention are closely analogous in structure and groupings to naturally occurring nucleosides and nucleotides. The essential chain arrangements and lengths are maintained. The appropriate O and OH functional groups, which in biological environments actively bind to biological centers, are maintained in their natural sequences and disposition relative to the base, but optionally modified with "protecting" groups. Indeed, the groups adjacent to the bases are so similar in chemical constitution to deoxyribose compounds that they can assume the essential conformation of the deoxyribose ring under appropriate conditions. The fundamental difference is that the compounds of the present invention lack the structural rigidity of carbohydrate ring, which renders them up predictably different in properties and behaviour. Also, the C-4' position is not chiral, in compounds of formula I, so that stereoisomers do not arise. Each hydroxyl is primary. There can be no syn-anti isomerism about the glycosidic bond.

DESCRIPTION OF THE PREFERRED EMBODIMENTS

The preferred bases X in the compounds of the present invention are the purine bases adenine and guanine. Compounds of adenine abound in nature, and show wide ranges of biological activity. It is among adenine and quanine compounds of the present invention that the most biologically active compounds are found. Test procedures for characterization and evaluation, e.g. with specific enzymes, are well established in connection with adenine compounds.

In contrast with natural adenosine compounds and most of the previously reported synthetic analogues thereof, the adenine compounds of the present invention are resistant to attack by adenosine deaminase enzymes found in most mammalian tissue, and deactivation thereby. Natural and previously reported synthetic analogues of adenosine compounds are attacked by this enzyme in vivo, with the result that the amine group at C6 on the prime ring is hydrolyzed to hydroxyl, forming the corresponding inosine compound, the majority of which are biologically inactive. With compounds subject to this reaction, the results of tests of biological activity carried out in vitro do not provide any useful guide to in vivo activity.

The compounds of the present invention, however, are very poor substrates for adenosine deaminase, and consequently do not deaminate in vivo, at least to any sigificant extent. Consequently, test results obtained in vitro are also obtainable in vivo.

Most preferred of compounds of formula I is that in which R and R' are both hydrogen and X is adenine or guanine, namely the compound of general fomula:

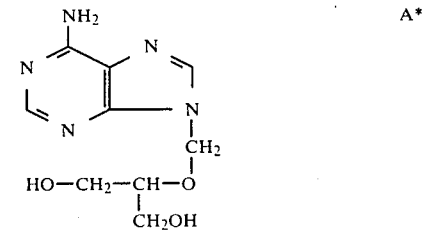

9-[[2-hydroxy-1-(hydroxymethyl)-ethoxy]-methyl]adenine, and the corresponding compounds in which one or both of R and R' represent dimethyl-tert.-butylsilyl, or of formula

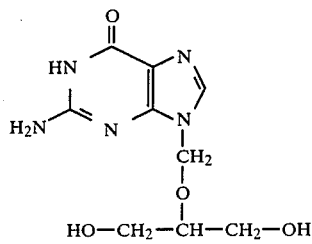

G*

Compounds of general formula I may be made by coupling the appropriately halogenated base with the appropriate alkyl residue. The synthesis may be initiated by treating 1,3-dichloro-2-propanol with sodium benzylate under a nitrogen atmosphere followed by trioxymethylene and HCL to prepare the chloromethoxy derivative, of 1,3-dibenzyloxy-2-propanol care being taken to remove excess water. This derivative may be coupled to the appropriately halogenated base, such as 6-chloropurine, in DMF using triethylamine as acid scavenger. Treatment of the chloro compound so formed with methanolic ammonia in a steel reaction bomb gives the 6-amino derivative. The product may be debenzylated to give a compound of formula I, e.g. with hydrogen over palladium oxide in methanol. Protecting groups, if desired, are put on by standard, known methods. Alaternatively, halogenated alkyl residues may be coupled with halogenated or non-halogenated purine or pyrimidine base compounds.

Several of the compounds of the present invention show anti-viral activity, accompanied by low cell toxicity, rendering them potentially useful in therapeutic compositions to combat specific viral invaders of living mammalian cells. For example, the compound 9-[[2-hydroxyl-1-(hydroxymethyl)-ethoxy]-methyl]adenine, is active against herpes simplex virus, influenza or virus, and against vesicular stomatitis virus. The compound G* (9-[[2-hydroxy-1-(hydroxymethyl)ethoxy]methyl]-guanine is extremely active against herpes simplex virus, and in fact shows an activity of magnitude much greater than that of acycloguanosine, as well as being active also against a broader range of viruses than acycloguanosine. Also, mono-O-tert-butyldimethyl silyl-9-[[2-hydroxy-1-(hydro v-methyl)ethoxy]-methyl]-adenine is active against influenza virus. In both cases, these compounds are active to combat the viruses, and prevent or at least substantially inhibit the replication thereof, at a dosage level at which they are non-toxic to mammalian cells.

Certain compounds of the aforementioned formula I in which the purine or pyrimidine base group X is substituted on the nucleus are also of interest as potential pharmacological agents e.g. anti-virals. Specific such compounds are those in which X represents uracil substituted at the 5-position with fluoro or hydroxymethyl; guanine or adenine substituted at the 8-position with halogen (especially but not limited to bromine), thio or amino, 5-fluorouracil, 5-aza-cytosine, 2-N-acetyl guanine, etc.

It will of course be understood that the present invention extends to cover pharmaceutically acceptable salts of the compounds described herein.

Compounds according to the present invention may be administered to a patient parenterally, interthecally applied topically as ointment, cream, aerosol or powder, or even on occasion given as eye or nose drops or orally. In general, methods of administration and dosage formulations thereof follow the known, published methods used with known antiviral drugs such as acycloguanosine, Ara-A and Ivdr. Effective unit doses for administration of the compositions interthecally or parenterally, calculated as free base, are suitably in the range from about 0.1–100 mg per k mammal body weight, most suitably in the 0.5–20 mg per kg mammal body weight, and most preferably about 5 mg per kg, on the basis of a dosage administered from 2–4 times per day.

Orally administrable compositions are preferably in fine powder or granule form, with diluting and/or dispersing and/or surface active agents, e.g. in water or in a syrup dispersion, or as tablets or capsules. Solutions of the compounds in distilled water or saline, e.g. isotonic solutions and optionally buffered with phosphate, of concentration 1–20% preferably 2–15% and most preferably around 10%, are suitable for parenteral or interthecal administration. Ointments (topical or cream) may be compounded for treatment of external infections, e.g. with an oil in water cream base, in a concentration of from about 0.1–10% preferably up to about 3%, most preferably about 1% w/v a tive ingredient. They may be compounded with paraffin oil, with petrolatum to form emulsion optionally with a surfactant for stabilizing purposes, or with dimethyl-sulfoxide.

The invention is further illustrated in the following non-limitative examples.

EXAMPLE 1

Preparation of 9-[[2-hydro-1-(hydroxymethyl)-ethoxy]methyl-]adenine(III)

6.5 m.moles of 6-chloropurine was condensed with 1,3-dibenzyloxy-2-chloromethoxypropane (6.5 m.moles) in dimethylformamide (4 ml) containing triethylamine (6.5 m.moles) at 25° C. for 16 hours. The product is formed, 1,3-dibenzyloxy-2-(6-chloropurine)-methoxy propane, was isolated from TLC plates as an oil, and subsequently heated in a steel bomb at 90° C. for 20 hours with 60 ml. methanol saturated (0° C.) with ammonia. The solvents were evaporated and 1,3-dibenzyloxy-2-adeninemethoxypropane obtained on precipitation from ethanol with ether. The compound was debenzylated using palladium oxide in methanol at 25 psi of hydrogen for 20 hours. The catalyst was removed by filtration, and on concentrating and cooling the methanol solution, the product 9-[[2-hydroxy-1-(hydroxymethyl)ethoxy]-methyl]-adenine (III) crystallized as a white solid. The overall yield from 6-chloropurine was 27% melting point 184°–186° C.

m/e (molecular weight) 239, $\lambda_{max}^{EtOH} = 259$ nm $R_f$ 0.12 (CHCl$_3$-Et OH, 4:1).

EXAMPLE 2

From compound III prepared according to Example 1, mono-O-tert.butyldimethyl silyl-9-[[2-hydroxyl-1-(hydroxymethyl)ethoxy]methyl]-adenine (compound X) and bis-O-tert.butyldimethyl silyl-9-[[2-hydroxy-1-(hydroxymethyl)ethoxy]methyl-adenine (compound XI) were prepared by reaction with appropriate controlled amounts of tert.butyl silyldimethyl chloride, in the standard manner for protection hydroxyl groups, according to methods of nucleoside synthesis, followed by standard procedures for separating the two products.

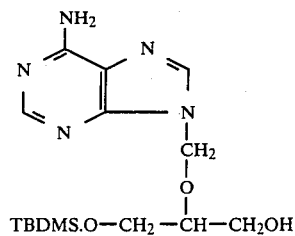

(X)

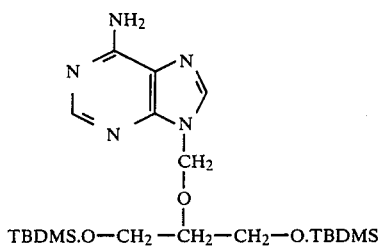

(XI)

where TBDMS represents tert.butyldimethylsilyl.

EXAMPLE 3

Compound III prepared according to Example 1 was tested for activity against viruses. The tests were conducted in the normal way growing mammalian cells in an appropriate medium on a culture disc. In the controls, viral cells were sprinkled onto the growing cell cultures and subsequent growth thereof observed. In the test experiments, both viral cells and compounds according to the invention were sprinkled onto the growing cell cultures.

The viral plaque growth was observed. Reduction in the numbers and size of the plagues growing on the cells indicates that the added compound is preventing the reproduction of the viruses.

Compound III was found to be active to inhibit reproduction of herpes simplex virus. At a dosage of 300 micrograms of compound per ml of medium, the plague area was reduced by 70%, without showing any evidence of toxicity towards the mammalian cells growing in the culture.

Compound III was also found to be active to prevent reproduction of the VSV (vesicular stomatitis virus), reducing the plaque numbers by 70% at a dosage of 1 mg per ml. Again, no evidence of toxicity to mammalian cells, at this same dosage level, was detected.

EXAMPLE 4

Compound X, prepared according to Example 2, was tested by the procedure described in Example 3 for activity against influenza A virus. It was tested at dosage levels of 0.1, 1.1 and 11 psg per ml, and at each of these levels was active to inhibit reproduction of the viral cells without demonstrating toxicity towards the mammalian cells. At higher dosage levels (110 micrograms per ml) it was toxic to the mammalian cells.

When compound X was similarly tested against the herpes simplex virus, it demonstrated toxicity towards mammalian cells at dosage level of 300 microg s/ml, without indicating selective activity against the virus.

Compound XI, in similar tests, indicated a very high level of toxicity towards the mammalian cells, at a dosage level of 30 micrograms per ml.

EXAMPLE 5

Preparation of 1-[[2-benzyloxy-1-(benzyloxymethyl)ethoxy]methyl]-5-fluorouracil

5-Fluorouracil (1.0 g, 0.0077 mole) and some crystals of ammonium sulfate were suspended in 1,1,1,3,3,3-hexamethyldisilazane (HMDS) (15 g) and brought to reflux with stirring. After 50 minutes the base had dissolved and the excess HMDS was evaporated under reduced pressure to yield syrup 15 of silyl-protected base (structure not determined). The syryp was dissolved in 1,2-dichloroethane (80 ml) and anh drous stannic chloride (0.4 ml) was added. 1,3-Dibenzyloxy-2-chloromethoxy propane (0.007 m mole) from a stock solution was added and the solution was stoppered and allowed to stand at room temperature overnight. The reaction mixture was shaken with aqueous sodium bicarbonate and the phases were separated. The aqueous phase was extracted with chloroform. The combined organic phases were washed once with water, dried with anhydrous sodium sulfate and evaporated under reduced pressure to yield 4.57 g of material. The nmr spectrum of the crude material suggested that the proportion of desired compound in the mixture was 88%. The material was mixed with 15 g of silica (Fisher-S-662) and applied to a silica column (93×2.0 cm). The column was eluted with 1% methanol in chloroform (250 ml), 3% methanol in chloroform (200 ml), and 5% methanol in chloroform (700 ml). When colored material began to appear fractions were collected and the first 16 test tubes contained the desired material. The fractions were individually evaporated to syrups which on standing overnight crystallized. Some methanol was added, the crystals were broken up and the solvent was removed with a pasteur pipet. The crystals were washed once with methanol to yield 0.886 g of crystals and 2.231 g of mother liquid residues. The residues were crystallized from carbon tetrachloride and the resultant mother liquor residues were applied to preparative tlc plates and eluted with 5% methanol in chloroform. Eventually 1.81 g (0.0044 mole, 62%) of crystalline 1-[[2-benzyloxy-1-(benzyloxymethyl)ethoxy]methyl]-5-fluorouracil was obtained. An analytical sample was obtained by recrystallizing the above material (tlc still showed an impurity) from a minimum of hot ethanol. The crystals gave: mp. 84°–86° C. and UV (EtOH) spectrum with $_{max}$265 nm.

The resultant compound, hereinafter referred to as 5F-benzyl-U*, has the structural formula:

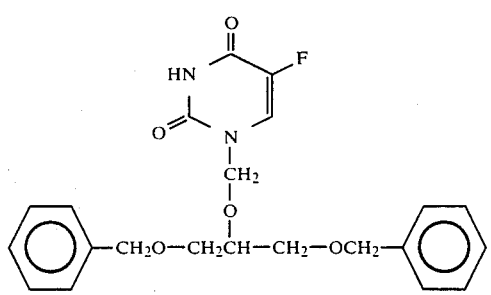

EXAMPLE 6

Preparation of 5-Fluoro-1-[[2-hydroxy-1-(hydroxymethyl)ethoxy]methyl]-uracil 5F-benzyl-U* prepared as described in Example 6, (0.656 g, 0.00158 mole) was dissolved in ethanol (26 ml). Fresh palladium black (10 ml) was added, followed by cyclohexane (13 ml). After half-hour, tlc showed that most of the starting material was gone but there was still a fair amount of monobenzyl compound present. After 5 hours tlc showed that the reaction was complete and the mixture was filtered and the Pd black was washed with ethanol. The solution was evaporated under reduced pressure to yield 0.413 g of syrup which crystallized after the addition of some methanol. The sample was dissolved in 3 ml of hot ethanol and then the volume was reduced to 1 ml by blowing with nitrogen. The resultant crystals (contained in a Greg tube) were washed 3 times with ethanol and the residual solvent was removed by centrifugation to yield 0.185 g (0.00079 mole, 50%) of crystals. The mother liquor yielded another 0.089 g (0.00038 mole, 24%) of crystals. A second recrystallization gave mp. 126°-128° C. and a UV spctrum (EtOH) $_{max}$266 nm. The nmr spectrum in DC$_3$OD and TMS gave: 3.58 (m, 5H, —CH$_2$CH CH$_2$—), 5.28 (s, 2H, OCH$_2$N.), 7.85 (d, 1H, J$_{F6}$=6.0 Hz, H-6).

The resultant compound, hereinafter referred to as 5FU*, has the structural formula:

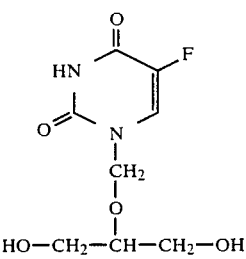

EXAMPLE 7

Preparation of 5-az-1-[[1-hydroxymethyl-[2-hydroxy]ethoxy]methyl]-cytosine

5-Azacytosine (5.0 g, 0.0446 mole) and some ammonium sulfate (100 mg) were suspended in HMDS (40 ml) and brought to reflux with stirring. After 20 minutes more ammonium sulfate was added and 20 minutes later the mixture became clear. The excess HMDS was evaporated under reduced pressure to yield a white solid, silyl-protected 5-azacytosine, which was used without further purification. The solid was dissolved in DCE (100 ml) and anhydrous stannic chloride (3.5 ml) was added. Then 1,3-dibenzyloxy-2-chloromethoxy propane (0.040 mole) was added and the solution was allowed to stand overnight at room temperature. The reaction solution was poured into aqueous bicarbonate, diluted with chloroform and shaken. The resultant precipitate was removed by filtration through celite. The phases were separated. The aqueous phase was extracted once with chloroform. The organic phases were combined, washed once with water, dried with anhydrous sodium sulfate and evaporated to yield 15 g of syrup. The syrup was dissolved in chloroform (20 ml) and applied to a tlc silica column (14.5×6.5 cm). The column was first eluted with chloroform (450 ml). The solvent was changed to 5% methanol in chloroform and the collection of fractions (10-15 ml) was begun. The desired compound 5-aza-1-[[2-benzyloxymethyl-[1-benzyloxy]-ethoxy]methyl]cytosine was found in three groupings of fractions which were: 40-42 (1.48 g), 43-62 (8.17 g) and 63-79 (0.42 g). The groupings were dissolved in 2.3 ml,12 ml and 1.5 ml of hot ethanol respectively and seeded. The second sample yielded 5.292 g of crystals whereas the other two samples gave few crystals. Therefore the first and third sample were combined with the mother liquor of the second sample and applied to a short silica column (4.0×6.3 cm) and first eluted with chloroform (125 ml) and then with 5% methanol in chloroform when the collection of fractions (20 ml) was begun. The desired material appeared in fractions 7-8 (1.35 g) and 9-11 (1.9 g). The 1.9 g sample was dissolved in ethanol (3 ml) and 0.917 g of crystals resulted. The yield of compound was 6.209 (0.0157, 39%). The crystals (6.209 g) were augmented by crystals (1.461 g) from another experiment and recrystallized from ethanol (10 ml) to give 6.95 g of white crystals. A sample was recrystallized twice from ethanol and it gave: mp 120°-122.5° C. The UV spectrum gave: $_{max}$(EtOH) 228, 236, (H$_2$O) 241, (pH 1) 251, (pH 13) 250. The nmr spectrum (CDCl$_3$) gave: 3.52 (d, 4H, J=5.5 Hz, CH$_2$CHCH$_2$—), 4.02 (m, 1H, —CH$_2$CHCH$_2$—), 4.45(s, 4H, 2×PhCH$_2$—), 5.30 (s, 2H, OCH$_2$N), 5.95 (bs, 1H, HNH(, 7.27 (m, 11H, 2×PhCH$_2$—, HNH), 8.07 (s, 1H, H-6).

The above produced compound 5-aza-1-[[2-benzyloxymethyl[1-benzyloxy]-ethoxy]methyl]cytosine (6.432 g), 0.0162 mole was dissolved in ethanol (200 ml, warmed). Used palladium oxide (8 g) was added followed by cyclohexene (100 ml). The stirred mixture was brought to reflux and 3 hours later tlc suggested that the reaction was slow. Therefore fresh palladium oxide (2 g) was added and reflux was continued. After a total time of 22 hours some material had precipitated out but the tlc still showed some starting material and the monobenzyl analogue. The material was filtered and the residue was washed with hot 95% ethanol until no more white precipitate was present. The filtrate and washings were combined and evaporated to yield about 4.5 g of material. The material was recrystallized from hot ethanol and some water (to help dissolve) to yield slightly greenish crystals (0.816 g, 0.00377 mole, 23.3%) which gave mp 181°-5° C. and the filtrate was green. The filtrate was evporated and the residue was dissolved in hot ethanol (3.5 ml) and seeded. Crystals did not form. The material was shaken with water and chloroform and the phases were separated. The aqueous phase was co-evaporated with ethanol to yield 2 g of material. Crystallization in the usual way was not successful. The tlc showed a number of components with the desired compound comprising about 30-40% of the mixture. The material was applied to 4 prep. tlc plates and developed with 50% methanol in chloroform. The desired band was eluted with 25% methanol in chloroform to yield 0.5 g of material. Crystallization in the usual way yielded only a trace of crystals. The first crop of crystals were recrystallized from water (1 ml) and ethanol (7 ml) to give white crystals which gave: mp 189.5°-191° C. the desired compound gave UV spectrum: $_{max}$(EtOH) 220 nm, (H$_2$O) 220, 245S, (pH 1) 250 (pH 13) 248. The nmr spectrum (CD$_3$OD+5 drops DMSO-d6+TMS) gave: 3.43-3.83 (m, 5H,—CH$_2$CHCH$_2$—), 5.37 (s, 2H, OCH$_2$N), 8.27 (s, 1H, H-6).

The resultant compound is 5-aza-1-[[1-hydroxymethyl[2-hydroxy]-ethoxy]methyl]cytosine, hereafter referred to as 5-aza-C*, has the structural formula:

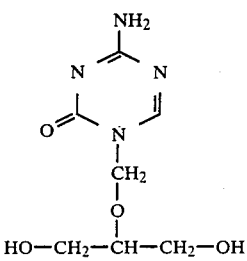

EXAMPLE 8

Preparation of 1-[[2-benzyloxy-1-(benzyloxymethyl)]ethoxymethyl]-cytosine

Cytosine 4 (5.0 g, 0.045 mole) was suspended in 1,1,1,3,3,3-hexamethyldisilazane (80 ml, 60 g HMDS) and several crystals of ammonium sulfate were added (molded on: G. Ritzmann & W. Pfleiderer, Chem. Ber. 106, 1401 (1973)). The stirred mixture was protected from moisture and refluxed until a clear solution was obtained. If a clear solution was not obtained after one-half hour of reflux the addition of more ammonium sulfate gave a clear solution after another 10 minutes of reflux. The clear hot solution was connected to a water aspirator and the excess HMDS was carefully removed on a hot water bath to yield a white solid which was used in the next step without purification.

The 2,4-bis-(trimethylsilyl)cytosine was dissolved in dry DCE (200 ml) and stannic chloride (3.4 ml, 29.1 moles anhydrous freshly distilled) was added. Then 40 g of stock chloride 3 solution (40 moles) was added and the yellow solution was allowed to stand overnight at room temperature (modeled on B. U. Niedballa & H. Verbruggen, Angew. Chem.

The resultant product is 1-[[2-benzyloxy-1-(benzyloxymethyl)]ethoxymethyl]cytosine, hereinafter referred to as dibenzyl C*, of structural formula:

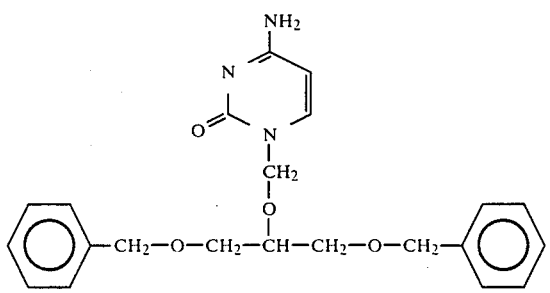

EXAMPLE 9

Preparation of 2-N-Acetyl-9-[[2-benzyloxy-1-(benzyloxymethyl)ethoxy]methyl]-guanine 2-N-Acetylguanine (1.93 g, 10 mmoles) and ammonium sulfate (100 mg) were suspended in HMDS (20 ml). The stirred mixture was refluxed for 3 hours when it became clear. The excess HMDS was removed under reduced pressure on a hot water bath to yield a white solid, silyl-protected 2-N-acetylguanine, which was used without further purification. The white solid was dissolved in DCE (50 ml) and 1,3-dibenzyloxy-2-chloromethoxy propane (5 mmoles) was added followed by freshly distilled anhydrous stannic chloride (1 ml). The solution was allowed to stand overnight at room temperature. The solution was poured into a mixture of aqueous sodium bicarbonate and chloroform and shaken. The mixture was filtered through celite to remove the precipitate. The phases were separated and the aqeous phase was extracted once with chloroform.

The combined organic phases were washed with water, dried with anhydrous sodium sulfate and evaporated under reduced pressure to yield 2.19 g of material. The reaction product was dissolved in chloroform (5 ml) and applied to a tlc silica column (9×6.5 cm). The column was first eluted with chloroform (60 ml) and then the solvent was changed to 2% methanol in chloroform. Three reasonably pure fractions were obtained from test tubes 15 (0.047 g), 19–20 (0.148 g) and 23–27 (0.43 g). Each of the samples were crystallized with ethanol and gave 20 mg., 64 mg and 250 mg of material respectively. On the basis of U.V. spectra the 250 mg material was determined to be 2-N-acetyl-9-[[2-benzyloxy-1-(benzyloxymethyl)ethoxy]meth l]guanine.

It was recrystallized from ethanol and gave m.p. 142°–4° C. The U.V. spectrum gave: max (EtOH)257,281 nm min 227,272, max (H$_2$O) 259,278 (shoulder), (pH1)262, (pH13)263.

The compound is hereinafter referred to as N-acetyl benzyl G*, and has the structural formula:

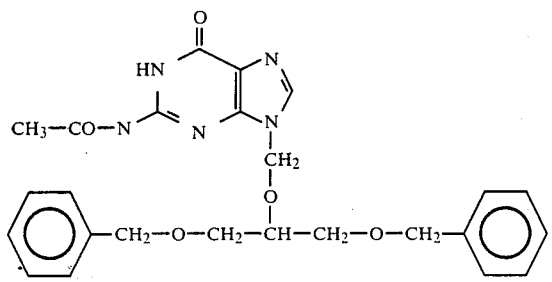

EXAMPLE 10

Preparation of 9-[[2-hydroxy-1-(hydroxymethyl)ethoxy]methyl]guanine

N-acetyl benzyl G* prepared as described in Example 10 (1.288 g, 0.00270 mole) was dissolved in pyridine (1.5 ml) andconcentrated ammonium hydroxide (6 ml) was added. The flask was tightly supported andput in a water bath set at 55° C. After 15 hours, crystals had precipitated which were filtered and washed with ethanol. The crystals gave m.p. 170°–177° C., were recrystallized from ethanol (60 ml) to yield 0.863 g (0.00191 mole, 70.7%) of 9-[[2-benzyloxy-1-(benzyloxymethyl)ethoxy]methyl]guanine, m.p. 180°–182° C.

The above prepared compound (0.665 g, 0.00139 mole) was dissolved in refluxing ethanol (40 ml). Palladium oxide (0.67 g) was added followed by cyclohexane (20 ml). Reflux was continued and after 2 hours tlc showed that there was still much starting compound present. Therefore more palladium oxide (0.6 g, Aldrich Gold Label). After 5.5 hours the reaction still seemed to progress slowly therefore palladium black (0.5 g—was stored several months under water and now dried by filtration and washing with ethanol) was added. After seven hours more cyclohexene (15 ml) was added. After 12 hours the reaction was not complete according to tlc but after 22.5 hours tlc showed that the reaction was complete. The reaction mixture was filtered hot and the catalyst was washed with hot 95 ethanol. Upon cooling crystals were deposited which were filtered and washed with 95% ethanol. The yield of crystals was 127 mg which did not melt up to 360° C. although they had become dark brown in colour. The catalyst still had product absorbed, and so it was washed with hot 75% ethanol. The washing was combined with the motor liquor from above and evaporated under reduced pressure. The residue was dissolved in a hot mixture of water (2.5 ml) and ethanol (2.5 ml) and then more ethanol (17.5 ml) was added with heating. The solution was allowed to crystallize. The crystals (155 mg) were filtered and washed with ethanol. The crystals did not melt up to 360° C. The mother liquor yielded about 60 mg of residue. Therefore the yield of product was 282 mg ((0.00110 mole, 79%). The UV spectrum gave: $_{max}$(EtOH), 254, 270 shoulder, (H$_2$O) 252, 269 (shoulder), (pH 1) 254, 272 (shoulder) (pH 13) 262.

The product is 9-[[2-hydroxy-1-(hydroxymethyl)ethoxy]methyl]guanine, hereinafter referred to as G*, of structural formula

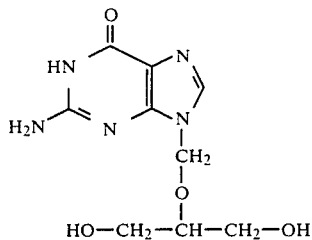

EXAMPLE 11

Testing and evaluation of compounds against herpes virus

Herpes simplex virus (HSV) strains were grown and titrated at 36° C. in human fetal fibroblasts derived from fetal tissues, and used for virus work before the tenth passage. Cells were grown and maintained in basal medium Eagle (BME; Auto-Pow, Flow Laboratories) supplemented with 0.112% sodium bicarbonate, mM 1-qlutanine, 2 mg neomycin per 100 ml and 5-20% calf serum. 5% BME, as described hereinafter, indicates medium containing 5 ml of calf serum in a total volume of 100 ml.

The titer of the HSV strains is determined by a plaque titration method (Roizman & Roane, "Virology", 15, 75–79, 1961). Tissue culture dishes are added with cells and used for assays when approximately 75% monolayer. Volumes (0.2 ml) of logarithmic dilutions of the strain are inoculated onto each of two tissue culture dishes, and absorbed for 1 hr. with intermittent shaking, the inoculum removed, and 2 ml of 5% BME containing 0.5% human immune serum globulin added. After a 48 hour incubation period at 36° C. in a 5% CO$_2$ atmosphere, the overlay medium is removed and the cell sheets stained with a 0.05% aqueous crystal violet solution. The number of plaques is counted, the duplicates averaged, and the number of plaque-forming units calculated.

The compounds are tested for activity against the herpes simplex strains using a stock solution of each compound freshly prepared by dissolving 1.2 mg in BME. Appropriate dilution of each compound are made in 5% BME containing 0.5% human immune serum globulin just before usage.

Tissue culture dishes (35 by 10 mm) with approximately 75% cell monolayer are inoculated with approximately 50 plaque-forming units of HSV per 0.2 ml, and the virus adsorbed for 1 hour, with intermittent shaking. After removal of the inoculum, 2 ml of 5% BME with 0.5% immune globulin and three-fold dilutions of the appropriate drug are added. One set of dishes receives no drug and is used as a control. After a 48-hour incubation period, at 36° C. in a 5% CO$_2$ atmosphere, the overlay medium is removed, the cells stained as described above, and plaques counted. The counts of replicate plates are averaged, and the number of plagues emerging in the presence of each drug dilution is calculated. The reduction in plaque size caused by the concentration of the drug, as compared with the relevant control, is also measured, visually. A reduction in plaque number indicates that the added compound is preventing the reproduction of the viral cells. A reduction in the area of the growing plaque indicates inhibition of plaque growth, i.e. inhibition of viral reproduction, caused by the drug.

The results showed that G*, the compound of example II, was outstandingly effective against herpes simplex. It reduced plaque size by 25% at concentrations as low as 0.02 ugm/ml, by 50% at 0.1 concentration and by 75% at 0.8 concentration. It reduced the plaque numbers by 25% at 0.04 ugm/ml, by 50% at 0.1 concentration and by 75% at 0.2 concentration. At the highest concentration level tested (250 ugm/ml) it showed no evidence of toxicity towards the cells. When the compound was used at concentrations of 2 ugm/ml and higher, no plaque formation or growth was detected. Significant activity was detected at concentrations as low as 0.007 ugm/ml.

The compound of example 8, 5-az-C*, also showed high activity against the HSV. It reduced plaque size by 25% at 5 ugm/ml, by 50% at 30 ugm/ml, and by 75% at 110 ugm/ml. It reduced plaque numbers by 25% at 8 ugm/ml, by 50 at 30 ugm/ml and by 75% at 140 ugm/ml. It showed no evidence of toxicity at concentrations as high as 304 ugm/ml.

The compound of example 9, dibenzyl-C*,m also exhibited activity against HSV, but to a lesser extent—25% plaque size reduction at 20 ugm/ml, 50% size reduction at 100 ugm/ml, 25% plaque number reduction at 20 ugm/ml and 50% plaque number reduction at 70 ugm/ml. The compound showed evidence of toxicity at concentrations of 305 ugm/ml.

The compound of example 6, 5F-benzyl-U*, showed activity against HSV, reducing plaque size by 25% at 10 ugm/ml, by 50% at 50 ugm/ml, and reducing plaque numbers by 25% at 70 ugm/ml, by 50% at 110 ugm/ml. It showed no evidence of toxicity up to concentrations of 110 ugm/ml.

The compound of example 10, N-acetyl-benzy G*, showed some activity against HSV, reducing plaque size by 25% at 60 ugm/ml, by 50% at 150 ugm/ml, and reducing plaque numbers by 25% at 20 ugm/ml, by 50% at 130 ugm/ml and by 75% at 310 ugm/ml.

Essentially similar results were obtained when compound G* was tested against 8 different strains of HSV type I, and 6 different strains of HSV type II.

EXAMPLE 12

Further testing and evaluation of compounds

The compounds produced as described above were tested by standard plaque titration methods to determine their activity against various other types of virus.

Tests for activity against the viruses were conducted as plaque tests, as described in Example 12 above. Compound G* showed activity against VSV at low concentrations, and against coxsackie virus CVB3 at low concentrations.

Compound G* was also tested against the virus Varicella Zoster, responsible for chicken pox and shingles infections in man, by similar procedures. It was found to be active against Varicella Zoster at concentrations as low as 13 ugm/ml.

I claim:

1. N-substituted pyrimidine compounds corresponding to the formula:

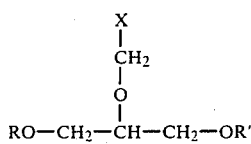

wherein X represents a uracil group, a 5-fluorouracil group, or a cytosine group; and R and R' are independently selected from hydrogen, benzyl and tert-butyldimethylsilyl.

2. Compounds according to claim 1, wherein X represents a pyrimidine moiety of formula

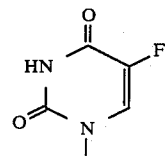

3. A compound according to claim 2, which is 1-[[2-benzyloxy-1-(benzyloxymethyl)ethoxy]methyl]-5-fluorouracil.

4. A compound according to claim 2, which is 5-Fluoro-1-[[2-hydroxy-1-(hydroxymethyl)ethoxy]methyl]-uracil.

5. Compounds according to claim 1 wherein X represents a pyrimidine moiety of formula

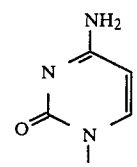

6. A compound according to claim 5 which is 1-[[2-benzyloxy-1-(benzyloxymethyl)]ethoxymethyl]cytosine.

7. A pharmaceutical composition suitable for administration to a mammal for treatment of viral infections, selected from the group consisting of herpes virus, influenza virus, and vesicular stomatitis virus, comprising as active ingredient 0.1 to 100 mg per kg of body weight, of a compound according to claim 1.

* * * * *